United States Patent [19]

Eastman et al.

[11] 4,064,190

[45] Dec. 20, 1977

[54] REMOVAL OF ACETYLENIC CONTAMINANTS BY COPPER-TIN AND/OR LEAD ZINC ALUMINATE

[75] Inventors: Alan D. Eastman; Floyd Farha, Jr., both of Bartlesville, Okla.

[73] Assignee: Phillips Petroleum Company, Bartlesville, Okla.

[21] Appl. No.: 751,499

[22] Filed: Dec. 17, 1976

[51] Int. Cl.$^2$ .............................................. C07C 7/00
[52] U.S. Cl. .......................... 260/681.5 R; 260/676 R; 260/677 A
[58] Field of Search ............. 260/681.5 R, 676, 677 A

[56] References Cited

U.S. PATENT DOCUMENTS

| | | | |
|---|---|---|---|
| 2,381,707 | 8/1945 | Wood et al. ........................ | 260/677 |
| 2,398,301 | 4/1946 | Frevel ................................ | 260/681.5 |
| 2,548,619 | 4/1951 | Ray .................................... | 260/677 |
| 2,636,911 | 4/1953 | Ray .................................... | 260/677 |
| 3,200,167 | 8/1965 | Reich ................................. | 260/681.5 |
| 3,541,178 | 11/1970 | Nehesheim ........................ | 260/681.5 |
| 3,634,536 | 1/1972 | Frevel et al. ..................... | 260/681.5 R |
| 3,636,127 | 1/1972 | Ramquist et al. .............. | 260/681.5 R |
| 3,754,050 | 8/1973 | Dugverman et al. ........... | 260/681.5 R |
| 3,758,603 | 9/1973 | Steigelmann et al. ......... | 260/681.5 R |
| 3,823,088 | 7/1974 | Box et al. ........................ | 210/63 |

*Primary Examiner*—Veronica O'Keefe

[57] ABSTRACT

Acetylenic compounds are selectively removed by conversion to innocuous materials by contacting hydrocarbon mixtures containing same with a copper-tin and/or lead-zinc aluminate catalyst. In one embodiment, acetylenic compounds are selectively removed from unsaturated hydrocarbon-containing mixtures in a cyclic process comprising alternate contact of the catalyst with a gaseous hydrocarbon phase containing acetylenic contaminants and thereafter of the catalyst with an oxygen-containing gas to regenerate the catalyst.

10 Claims, No Drawings

REMOVAL OF ACETYLENIC CONTAMINANTS BY COPPER-TIN AND/OR LEAD ZINC ALUMINATE

This invention relates to the purification of unsaturated hydrocarbon mixtures to remove undesirable acetylenic contaminants therefrom. In accordance with one aspect, this invention relates to a process of removing unsaturants such as acetylenes from hydrocarbon mixtures containing same by converting the acetylenic compounds to innocuous materials by contacting with a copper-tin and/or lead-zinc aluminate catalyst under conditions to selectively remove and/or convert the acetylenic compounds. In accordance with a further aspect, this invention relates to a process for the purification of unsaturated hydrocarbon-containing mixtures also containing acetylenic compounds as impurities by contacting at an elevated temperature with a catalyst of zinc aluminate promoted with copper, tin, and/or lead under oxidizing conditions. In accordance with a further aspect, this invention relates to a cyclic process for the purification of an unsaturated hydrocarbon-containing mixture also containing acetylenic contaminants by alternately contacting a copper-tin and/or lead-zinc aluminate catalyst with the hydrocarbon-containing mixture and an oxygen-containing gas to reactivate the catalyst and extend catalyst life. In accordance with a further aspect, this invention relates to a process for the selective removal of acetylenic contaminants in unsaturated hydrocarbon-containing mixtures by contacting the mixture with a copper-tin and/or lead-zinc aluminate catalyst in the presence of hydrogen under mild conditions of temperature.

The present invention provides a method whereby acetylenes such as vinylacetylene, methylacetylene, 1-butyne, and the like can be selectively removed from hydrocarbon mixtures containing same, especially unsaturated hydrocarbon mixtures containing them, without the necessity for hydrogenation and extensive fractionation. There is thus provided a means whereby substantial reduction and planned investment in utilities are realized.

The invention relates more specifically to a process for removing acetylenic compounds (impurities) found in small amounts, i.e. 0.01-3 mole percent in refinery streams comprising paraffins, olefins, diolefins, water, nitrogen, oxygen, etc. The product gas stream obtained by the vapor phase catalytic oxidation of butenes to form 1,3-butadiene is a typical stream which can be treated by the process of the present invention. Such a gas stream contains, in addition to 1,3-butadiene, unreacted butene, water, oxygen, nitrogen, carbon dioxide, carbon monoxide, and traces of acetylenes. The presence of acetylenes in the product is most undesirable, causing difficulties in the subsequent separation of 1,3-butadiene from unreacted butenes and being an unacceptable impurity in the final product.

It has now been found that by selective oxidation in the presence of a copper-tin and/or lead-zinc aluminate catalyst it is possible to remove the acetylenes from such gaseous streams without significant loss of other unsaturated hydrocarbons by oxidation.

Accordingly, an object of this invention is to provide a simplified process for removing acetylenes from unsaturated hydrocarbon-containing mixtures such as conjugated diene streams.

Another object of this invention is to provide an improved process for removing acetylenes from conjugated diene-containing mixtures to provide a highly purified conjugated diene-containing stream.

A further object of this invention is to provide a process for purification of conjugated diene streams obtained from oxidative dehydrogenation processes whereby acetylenic contaminants are removed therefrom.

Other objects and aspects, as well as the several advantages of this invention, will be apparent to those skilled in the art upon a study of the disclosure and the appended claims.

According to the present invention, a process is provided for the removal and/or conversion to innocuous materials of acetylenic compounds from a gas stream containing same which comprises contacting the gas stream with a copper-tin and/or lead-zinc aluminate catalyst under conditions of temperature and pressure sufficient to substantially remove the acetylenes present without significant destruction of desirable unsaturated hydrocarbons in the stream being treated. More specifically, according to the invention, acetylenic compounds in hydrocarbon-containing streams, especially unsaturated hydrocarbon-containing streams, are removed by selective oxidation reaction conditions by contacting with a copper-tin and/or lead-zinc aluminate catalyst.

Further in accordance with the invention, acetylenic compounds in unsaturated hydrocarbon-containing streams are removed by contacting with a copper-tin and/or lead-zinc aluminate catalyst in the presence of hydrogen under mild conditions of temperature.

In actual operation, small amounts of acetylenes, i.e., 0.01-3 mole percent, contained in refinery streams or other hydrocarbon streams comprising olefins, diolefins, paraffins, water, nitrogen, etc., are selectively removed under reaction conditions with the catalysts of this invention. The acetylenes are selectively oxidized to water and carbon oxides in the presence of oxygen contained in solid catalysts comprising combined copper, tin, and/or lead, and oxygen supported on zinc aluminate. In a cyclic process, the oxygen is supplied from combined oxygen in the catalyst. In a continuous process, free oxygen is added to the feed. Under mild conditions (about 300° F–400° F) when hydrogen is present, the acetylenes can be selectively hydrogenated.

In general, the catalysts are prepared by impregnation of zinc aluminate with a solution containing one or more of the promoting metal compounds. It is convenient to include all of the metal components for a given catalyst in one solution although, optionally, sequential impregnation can also be practiced. In addition, dry mixing of the support with solid compounds of the promoter metal compounds can be used in an alternative method of preparation. Suitable metal compounds employed are preferably those which are convertible to the metal oxide or to the metal when the compositions are calcined in air. Exemplary compounds include the carbonates, hydroxides, nitrates, oxalates, and oxides of copper, tin, and lead, as well as salts of those metals with carboxylic acids such as acetic, citric, formic, tartaric, and the like. The resulting compositions are dried when necessary and calcined in air for about 30 minutes to 20 hours or more at temperatures ranging from about 500° F to 1600° F (260°–871° C), more preferably from about 875° F–1500° F (468°–816° C). The products, after cooling, can be ground and screened, and utilized in the form of particles ranging in size from about 4 to about 40 mesh (U.S. Sieve Series). If desired, the powdered catalysts can also be formed into pellets, wafer, cylinder, etc., ranging in size from about 1/32 to ½ inch (0.08–1.3 cm) by means of conventional pelleting methods. When lubricants are used, the composites are generally calcined. They can be used as such or ground and sieved. The finished, calcined catalysts have surface areas ranging from about 5–100 square meters per gram.

The concentration of promoter metals on zinc aluminate, after calcination and calculated as the metals, is generally in the range of 0.1 to 20 weight percent, preferably 1–10 weight percent, based on the weight of zinc aluminate plus the metal promoters present. The weight ratio of Cu/Sn or Cu/Pb is preferably about 4:1 although it can vary from about 1:1 to about 10:1.

The process of the invention can be carried out under a wide range of conditions, depending upon the feedstock, catalyst, and desired degree of acetylenes removal. The reaction is carried out in a continuous or cyclic fashion, more preferably cyclic, with a fixed catalyst bed as the preferred mode of operation. However, the cyclic process of this invention can be carried out by means of any apparatus whereby there is obtained alternate contact of the catalyst with the gaseous phase containing the hydrocarbon-containing stream and thereafter of the catalyst with the oxygen-containing gaseous phase. In such an operation, air or an oxygen-containing stream and the feed are alternately passed over the catalyst bed. In a continuous process, sufficient oxygen is included with the feed to insure that all or substantially all of the acetylenes present are selectively oxidized. By sufficient oxygen is meant an oxygen to total hydrocarbon mole ratio ranging from about 0.01–0.3:1 is required.

Suitable reaction conditions for treatment of the feed include temperatures ranging from about 250°–800° F (121°–427° C), more preferably from about 300°–650° F (149°–343° C); reaction pressures ranging from about 0.5–500 psig (3.4–3450 kPa gage), more preferably from about 5–100 psig (34–690 kPa gage); and a stream to hydrocarbon mole ratio of 0 to 100, more preferably 0 to 50. Hydrocarbon feed rates can range from about 50 to about 5000 gaeous hourly space velocity (GHSV). Reaction times can range from about 0.01 to 10 minutes, preferably from 0.02 to 5 minutes. The amount of oxygen supplied by the catalyst during the reaction generally amounts to from about 0.05 to about 10 weight percent of the combined oxygen in the catalyst, depending upon the reaction conditions and catalyst employed.

Reoxidation of spent catalyst in the regeneration step generally requires from about 1 to about 10 times the reaction period. Regeneration can be effected in situ by cutting off the hydrocarbon feed and admitting oxygen or an oxygen-containing gas at a somewhat elevated temperature compared to the reaction temperature. Regeneration temperatures can range from about 100° to about 300° F (38°–149° C) higher than the process temperatures employed to maintain selectivity to oxidation of acetylenes. When process temperatures and regeneration temperatures are about the same, selectivity to acetylenes oxidation decreases rapidly.

At the conclusion of the regeneration period, the oxygen supply is discontinued and the oxygen in the system is thoroughly purged out with an inert gas or mixture of gases. Casual mixing of the feed stream and regeneration stream is avoided. Gaseous diluents such as stream and other gases such as nitrogen, helium, argon, and the like optionally can be present during regeneration and/or during treatment of the feed.

As indicated above, it is also within the scope of the invention to selectively remove acetylenic compounds present in unsaturated hydrocarbon-containing streams by contacting such streams with the instant catalyst under mild conditions of temperature in the presence of hydrogen. Suitable conditions of temperature for carrying out this aspect of the invention range from about 300° F to about 400° F. The amount of hydrogen present can vary appreciably but the hydrogen to acetylene mole ratio will generally be in the range of 1.1:1 to 100:1. The hydrogenation reaction is carried out in a continuous fashion with a fixed bed of catalyst as the preferred mode of operation, as described herein in connection with oxidation but in the substantial absence of added oxygen.

EXAMPLE I

Catalyst Preparations

Invention catalyst A was prepared by impregnating a sample of zinc aluminate (6–16 mesh particles, U.S. Sieve Series) containing about 1 weight percent tin as tin oxide ($SnO_2$) with an aqueous solution of cupric nitrate sufficient to provide about 4 weight percent copper on the dry composite. The composite was dried at 120° C and calcined for 5 hours at 1800° F (982° C) in air. The tin-zinc aluminate base was prepared by vigorously stirring a mixture of 425 g powdered alumina, 362 g powdered zinc oxide, and 10 g powdered tin oxide ($SnO_2$) dispersed in 1750 ml deionized water for about 1 hour. The slurry was then ball milled for 2 hours, dried at 110° C in a forced draft oven and ground to pass to 40-mesh screen. The ground material was mixed with 5 weight percent powdered polyethylene and formed into tablets measuring ¼ inch diameter (0.6 cm) by 0.09 inch (0.2 cm) long with a conventional tableting machine. The tablets were calcined in air for 1 hour at 800° F (427° C), 1 hour at 1000° F (538° C), 1 hour at 1100° F (593° C), and 3 hours at 1875° F (1024° C), cooled, and ground into particles. A sample of the fraction consisting of 6–16 mesh particles was used to prepare the catalyst. Invention catalyst A had an apparent bulk density of 0.85 g/cc, and a surface area of 33.7 $m^2/g$. Analysis showed it to contain 4.3 weight percent copper in the form of copper oxide and 0.98 weight percent tin in the form of tin oxide dispersed on zinc aluminate.

Invention catalyst B was prepared by impregnating a sample of 6–16 mesh particles of zinc aluminate containing 1 weight percent lead oxide with an aqueous solution of cupric nitrate sufficient to provide 4 weight percent copper on the dry composite. The composite was dried at 120° C and calcined in air for 3 hours at 1830° F (999° C). The lead-zinc aluminate base was prepared by vigorously stirring a mixture of 425 g powdered alumina, 362 g powdered zinc oxide, and 7.9 g powdered lead oxide (PbO) dispersed in 1750 ml deionized water for one-half hour. Therafter, the slurry was ball milled, ground, mixed with 6 weight percent powdered polyethylene, pelleted, calcined, and ground into 6–16 mesh particles in the manner described for invention catalyst A. Invention catalyst B was calculated to contain 4 weight percent copper in the form of copper oxide and 0.9 weight percent lead as PbO (1 weight percent PbO) dispersed on zinc aluminate.

Invention catalyst C was prepared by vigorously mixing 40 g powdered alumina, 34 g powdered zinc oxide, 1.9 g powdered cupric oxide, and 0.5 g powdered tin oxide ($SnO_2$) in 250 ml deionized water for 15 minutes. The slurry was dried in a forced draft oven at 140° C and ground to pass a 40-mesh screen. The product was mixed with 3.9 weight percent powdered polyethylene, and, as in invention catalyst A, was formed into tablets, calcined, and ground into 6-16 mesh particles. Invention catalyst C was calculated to contain 2 weight percent copper as copper oxide and 0.5 weight percent tin as tin oxide dispersed on zinc aluminate.

Control catalyst D was formed by impregnating zinc aluminate with an aqueous solution of cupric nitrate sufficient to add 4 weight percent copper based on the dry weight of the composite. The composite was dried overnight at 120° C and calcined for 2 hours at 800° F (427° C) and 4 hours at 1000° F (538° C). The cooled product was ground into 6-16 mesh particles.

A 3 cc sample of each catalyst was charged to a fixed bed automated testing unit, and the reactor and catalyst was brought up to the process temperature employed in that test in the presence of nitrogen. Steam was not present unless specified otherwise. Each cycle consisted as follows: nitrogen was cut off and the feed passed to the reactor for one-fourth of the cycle time noted in Table I. The feed was stopped and nitrogen at about 650 GHSV was used to flush the catalyst and reactor for one-fourth the cycle time as the temperature was raised to the desired regeneration temperature. The nitrogen was cut off and air at about 650 GHSV was passed over the catalyst for one-fourth the cycle time to regenerate it. The air was then cut off and catalyst and reactor purged with about 650 GHSV nitrogen for one-fourth the cycle time as the temperature was lowered to the process temperature to complete cycle one.

The feed used and effluents obtained were analyzed by means of gas-liquid chromatography. A typical feed analysis and an effluent analysis adjusted on an air and nitrogen flush-free basis for Run 2 in Table I are given below.

Control runs 9 and 10 were operated in a continuous process with free oxygen added. In these runs, an oxygen to total hydrocarbon mole ratio of 0.2:1 was employed. In addition, in run 10, a steam to hydrocarbon mole ratio of 12.3:1 was employed.

| $C_4$ Refinery Stream Feed Component, Mole Percent | | Effluent Component, Mole Percent |
|---|---|---|
| Oxygen | — | — |
| Nitrogen | 0.603 | 0.892 |
| Carbon dioxide | 0.018 | 0.339 |
| Methane | — | — |
| Ethane, ethylene | 0.140 | 0.095 |
| Propane | 0.184 | 0.058 |
| Propylene | 1.032 | 0.361 |
| Isobutane | 1.651 | 1.346 |
| n-Butane | 7.679 | 7.928 |
| Neopentane | — | 0.009 |
| Butene-1 | 38.921 | 39.030 |
| t-Butene-2 | 5.958 | 6.315 |
| c-Butene-2 | 6.510 | 6.947 |
| 1,3-Butadiene | 36.749 | 36.533 |
| Isopentane | — | — |
| 3-Methylbutene-1 | — | — |
| n-Pentane | 0.039 | 0.043 |
| Pentene-1 | — | 0.106 |
| t-Pentene-2 | — | — |
| c-Pentene-2 | 0.043 | — |
| 2-Methylbutene | — | — |
| Vinylacetylene | 0.378 | — |
| | 99.905 | 100.002 |

The conditions employed and results obtained are given in Table I.

Table I

Selective Conversion of Vinylacetylene in Streams Comprising $C_4$ Hydrocarbons

| Run No. | Catalyst, Wt. % | | | Process/Regen. Temperature | | Feed GHSV | No. of Cycles when Sampled | Cycle Length Min. | Conversion, Mole % | | | Remarks |
|---|---|---|---|---|---|---|---|---|---|---|---|---|
| | Cu | Sn | Pb | °F | °C | | | | VAC[3] | Buta.[4] | Butenes | |
| 1 | 4.3 | 0.98 | 0 | 400/500 | 204/260 | 650 | 2 | 80 | 86 | 0.53 | −1.7 | [1] |
| 2 | 4.3 | 0.98 | 0 | 400/550 | 204/288 | 650 | 8 | 80 | 100 | 0.59 | −1.8 | |
| 3 | 4.3 | 0.98 | 0 | 350/500 | 177/260 | 1300 | 48 | 60 | 100 | 10 | 10 | Life test |
| 4 | 4.3 | 0.98 | 0 | 350/500 | 177/260 | 1300 | 168 | 60 | 100 | 24 | 3.8 | Life test |
| 5 | 4.3 | 0.98 | 0 | 350/500 | 177/260 | 1300 | 238 | 60 | 39 | 6.6 | 3.4 | Life test |
| 6 | 4 | 0 | 0.9 | 400/500 | 204/260 | 650 | 3 | 80 | 100 | 6.1 | 1.4 | |
| 7 | 4.3 | 0.98 | 0 | 350/550 | 177/288 | 650 | 3 | 80 | 100 | 7.3 | 5.2 | |
| 8 | 4 | 1 | 0 | 350/500 | 177/260 | 650 | 55 | 80 | 100 | 15.6 | 14 | |
| 9 | 4 | 1 | 0 | 500 cont. | 260 | 650 | — | — | 94 | 4.2 | −0.1 | |
| 10 | 0 | 0 | 0 | 550 cont. | 288 | 1300 | — | — | 11 | 2.2 | 1.5 | Control, $ZnAl_2O_4$ catalyst. |
| 11 | 0 | 0 | 0 | 350/500 | 177/260 | 1300 | 3 | 60 | 81 | 0.7 | 1.0 | Control, $ZnAl_2O_4$ catalyst. |
| 12 | 4 | 0 | 0 | 600/750 | 316/399 | 650 | 2 | 60 | 100 | 0.9 | −0.8 | Control |
| 13 | 4 | 0 | 0 | 600/750 | 316/399 | 650 | 14 | 60 | 31 | 0.8 | −1.3 | Control[2] |
| 14 | 2 | 0.5 | 0 | 500/650 | 260/343 | 650 | 1.8 | 60 | 100 | 4.5 | 0.7 | |

[1]Regeneration temperature is too low, some VAC is present. Minus sign under butenes indicates net formation of butenes.
[2]Catalyst is not regenerating at these conditions as low VAC conversion shows.
[3]Vinylacetylene.
[4]1,3-Butadiene.

The results show that zinc aluminate itself is not an effective catalyst under the continuous conditions employed in control run 10. When employed in a cyclic process, however, zinc aluminate in control run 11 converts 81 percent of the vinylacetylene after three cycles. Under similar reaction conditions and even after 168 cycles, the copper/tin/zinc aluminate catalyst of invention run 4 still converts 100 percent of the vinylacetylene to oxidation products. However, as run 5 shows, this invention catalyst has diminished capacity for vinylacetylene removal under the conditions employed after 238 cycles. In comparing inventions runs 1 and 6, it can be seen, based on vinylacetylene conversion, that at process/regeneration temperatures of 400°/500° F the copper/tin/zinc aluminate catalyst is less active than the copper/lead/zinc aluminate catalyst. The copper/tin/zinc aluminate catalyst requires about a 150° F or higher regeneration temperature than process temperature to give 100 percent vinylacetylene conversion. This is demonstrated in invention runs 2 and 7. Thus, a spread of at least about 150° F is necessary to maintain an active copper/tin/zinc aluminate catalyst in a cyclic process whereas a spread of about 100° F is sufficient for a copper/lead/zinc aluminate catalyst at similar metal contents. Control runs 12 and 13 suggest that when tin or lead is not included with copper and zinc aluminate the catalyst rapidly loses activity in a cyclic process. Invention run 14 demonstrates that the quantity of copper and tin can be halved, although the Cu/Sn weight ratio is the same, and an active catalyst still results. Run 9 shows that the invention catalysts can be employed in a continuous process at 500° F to remove 94 percent of the vinylacetylene.

EXAMPLE II

A synthetic stream consisting primarily of ethylene admixed with a little propane and acetylene and a refinery stream comprising ethylene, methane, ethane, hydrogen, and acetylene were tested for acetylene removal in a cyclic process using several invention catalysts in the manner described in Example I. The feeds and effluents obtained were analyzed by means of gas-liquid chromatography with the analyses given below. The conditions employed and results obtained are summarized in Table II.

| Synthetic Feed Runs 1-4 | | Effluent, Mole % | | | |
|---|---|---|---|---|---|
| | Mole % | Runs: 1 | 2 | 3 | 4 |
| Oxygen | — | — | — | — | — |
| Nitrogen | — | — | — | — | — |
| Carbon monoxide | — | — | 0.044 | 0.037 | — |
| Carbon dioxide | — | — | — | — | — |
| Ethane | — | — | — | — | — |
| Ethylene | 99.593 | 99.348 | 97.110 | 99.468 | 99.803 |
| Propane | 0.032 | 0.144 | 0.151 | 0.260 | 0.144 |
| Propylene | — | — | — | — | — |
| Acetylene | 0.374 | — | 0.040 | — | — |
| $C_4$'s | — | 0.508 | 2.653 | 0.265 | 0.052 |
| | 99.999 | 100.000 | 99.998 | 100.000 | 99.999 |

An invention catalyst was also tested for acetylene removal in a continuous process (runs 2 and 3) including sufficient air with the feed to give an oxygen to total hydrocarbon mole ratio of 0.2:1.

| Refinery Feed, Run 5, Mole % | | Effluent, Mole %, Run 5 |
|---|---|---|
| Hydrogen | 15.634 | 18.374 |
| Carbon monoxide | 0.139 | 0.121 |
| Carbon dioxide | — | — |
| Methane | 11.485 | 3.333 |
| Ethane | 7.484 | 7.941 |
| Ethylene | 64.511 | 68.783 |
| Propane | 0.116 | 0.113 |
| Propylene | 0.124 | 0.133 |
| Acetylene | 0.166 | — |
| $C_4$'s | 0.342 | 1.201 |
| | 100.001 | 99.999 |

CO. It appears that the cyclic process is more efficient at low process temperatures than the continuous process since 100 percent acetylene conversion was obtained with the synthetic feed at 350° F was required for the continuous process. Run 5 demonstrates that refinery $C_2$ streams comprising ethylene, acetylene, etc., can be treated at temperatures as low as 300° F in a cyclic process with the invention catalysts to remove 100 percent of the contained acetylene.

We claim:

1. A process for the selective removal of acetylenic contaminants or impurities present in hydrocarbon streams which comprises contacting a hydrocarbon-containing mixture contaminated with acetylenic compounds with a catalyst consisting essentially of zinc aluminate promoted with copper and at least one of tin and lead in which the total concentration of promoter metals present, calculated as the metals, ranges from about 0.1 to about 20 weight percent based on the weight of zinc aluminate plus metal promoters under reaction conditions including an elevated temperature sufficient to selectively remove a substantial portion of said acetylenic compounds present in said mixture.

2. A process according to claim 1 wherein said contacting is effected at a temperature in the range of about 250°–800° F (121°–427° C), a reaction pressure in the range of about 0.5–500 psig (3.4–3447 kPa gage), and a hydrocarbon feed rate ranging from about 50 to about 5000 GHSV.

3. A process according to claim 1 wherein said hydrocarbon-containing mixture comprises olefins, diolefins, paraffins, and the like, and said contacting is effected in a continuous manner in the presence of an oxygen-containing gas at an oxygen to total hydrocarbon mole ratio of about 0.01–0.3:1.

4. A process according to claim 1 wherein said contacting is effected in a continuous manner in the presence of air at an oxygen to hydrocarbon mole ratio of about 0.01–0.3:1, steam at a steam to hydrocarbon mole ratio up to about 100, and at a temperature in the range of about 400°–650° F (204°–343° C).

5. A process according to claim 1 wherein said mixture is a mixture of unsaturated hydrocarbons obtained as the effluent from the oxidative dehydrogenation of olefins and the effluent contains steam and acetylenes, as well as 1,3-butadiene and other saturated and unsaturated hydrocarbons, and said contacting is effected at a temperature in the range of about 400°–650° F (204°–343° C).

6. A process according to claim 1 wherein zinc alumi-

TABLE II

Selective Conversion of Acetylene in Streams Comprising $C_2$ Hydrocarbons

| Run No. | Catalyst, Wt. % | | | Process/Regen. Temperature | | Feed GHSV | No. of Cycles when Sampled | Cycle Length Min. | Conversion, Mole % | | Remarks |
|---|---|---|---|---|---|---|---|---|---|---|---|
| | Cu | Sn | Pb | ° F | ° C | | | | Acet. | Ethylene | |
| 1 | 4 | 0 | 0.9 | 400/500 | 204/260 | 650 | 3 | 40 | 100 | 0.25 | Invention. |
| 2 | 4 | 0 | 0.9 | 500/— | 260/— | 650 | — | — | 89 | 2.5 | Control, cont. process, sampled at 2 hours. |
| 3 | 4 | 0 | 0.9 | 550/— | 288/— | 650 | — | — | 100 | 0.13 | Control, cont. process, sampled at 3 hours. |
| 4 | 4 | 0 | 0.9 | 350/400 | 177/204 | 650 | 3 | 40 | 100 | −0.21[1] | Invention. |
| 5 | 4.3 | 0.98 | 0 | 300/400 | 149/204 | 650 | 3 | 60 | 100 | −6.6 | Invention. |

[1]Minus indicates formation of additional ethylene. For Runs 1 and 4, a cycle consists of 10 minutes feed, 10 minutes nitrogen purge, 10 minutes air regeneration, and 10 minutes nitrogen purge. In Run 5, a cycle consisted of 20 minutes feed, 10 minutes nitrogen purge, 20 minutes air regeneration, and 10 minutes nitrogen purge.

Inspection of the data presented show that the invention catalysts are capable of converting from 89 to 100 percent of the acetylene present in the $C_2$ feed streams under the conditions employed to either ethylene or nate is promoted with about 1–10 weight percent of the promoter metals and the contacting is effected in a continuous manner in the presence of air at an oxygen to hydrocarbon mole ratio of about 0.01–0.3:1, steam to a steam to hydrocarbon mole ratio of about 10 to about 50, and at a temperature in the range of about 400°–650° F (204°–343° C).

7. A process according to claim 1 wherein said mixture comprises a mixture of unsaturated $C_4$ hydrocarbons including 1,3-butadiene and said catalyst is zinc aluminate promoted with about 1–10 weight percent of said promoter metals.

8. A process according to claim 1 wherein said contacting is carried out in a continuous manner in the presence of hydrogen at a mole ratio of hydrogen to acetylene ranging from 1.1:1 to 100:1 and at a temperature in the range of about 300° F to about 400° F (149°–204° C).

9. A process according to claim 1 for selectively converting acetylenic compounds to innocuous materials in a cyclic process which comprises alternately contacting said catalyst with said hydrocarbon feed and then an oxygen-containing gas under conditions to regenerate said catalyst, and repeating said alternate contacting.

10. A process according to claim 9 wherein the conditions during regeneration include a temperature ranging from about 100° F to about 300° F higher than the process temperature employed to maintain a high selectivity of oxidation of acetylenic compounds.

* * * * *